(12) United States Patent
Rigney

(10) Patent No.: US 7,289,911 B1
(45) Date of Patent: Oct. 30, 2007

(54) SYSTEM, METHODS, AND COMPUTER PROGRAM PRODUCT FOR ANALYZING MICROARRAY DATA

(76) Inventor: David Roth Rigney, 2004#B Ann Arbor Ave., Austin, TX (US) 78704

( * ) Notice: Subject to any disclaimer, the term of this patent is extended or adjusted under 35 U.S.C. 154(b) by 0 days.

(21) Appl. No.: 09/934,156

(22) Filed: Aug. 21, 2001

Related U.S. Application Data

(60) Provisional application No. 60/227,421, filed on Aug. 23, 2000.

(51) Int. Cl.
*G01N 33/48* (2006.01)

(52) U.S. Cl. ...................................................... 702/19

(58) Field of Classification Search .................. 702/19
See application file for complete search history.

(56) References Cited

U.S. PATENT DOCUMENTS

| 6,245,517 B1 | 6/2001 | Chen et al. |
| 6,263,287 B1 | 7/2001 | Zheng et al. |

OTHER PUBLICATIONS

Andrade et al., Bioinformatics, vol. 15, pp. 391-412, 1999.*
McCallum, www-2.cs.cmu.edu/~mccallum/bow/rainbow, pp. 1-11, 1998.*
Benson et al., Nucleic Acids Research, vol. 25, pp. 1-6, 1997.*
Bairoch et al., Nucleic Acids Research, vol. 25, pp. 217-221, 1997.*
Duggan, D.J., M. Bittner, Y. Chen, P. Meltzer and J.M. Trent. Expression profiling using cDNA arrays. Nature Genetics 21, Suppl 1: 10-14 (1999).
Newton, M.A., C.M. Kendziorski, C.S. Richmond, F.R. Blattner, and K.W. Tsui. On differential variability of expression ratios. Tech. Rept. 139, Dept. of Biostatistics, Univ. of Wisconsin-Madison. http://www.stat.wisc.edu/~newton/papers/publications (1999).
Iyer, V.R., M.B. Eisen, D.T. Ross, G. Schuler, T. Moore, J.C.F. Lee, J.M. Trent, L.M. Staudt, J. Hudson Jr., M.S. Boguski, D. Lashkari, D. Shalon, D. Botstein and P.O. Brown. The transcriptional program in the response of human fibroblasts to serum. Science 283: 83-87 (1999).
Eisen, M.B, P.T. Spellman, P.O. Brown and D. Botstein. Cluster analysis and display of genome-wide expression patterns. Proc Natl Acad Sci USA 95: 14863-14868 (1998).
Tavazoie, S., J.D. Hughes, M.J. Campbell, R.J. Cho, and J.M. Church. Systematic determination of genetic network architecture. Nature Genetics 22:281-285 (1999).

(Continued)

*Primary Examiner*—Cheyne D Ly

(57) ABSTRACT

The present invention relates to systems, methods, and computer program products for the analysis of gene expression data, especially data that have been acquired using microarray technologies. The present invention relates to methods for partitioning a set of genes into clusters, based on the similarity of the genes' rates of messenger RNA synthesis. The present invention also relates to methods for annotating clusters with words or phrases that are extracted from documents associated with genes in the clusters. The present invention also relates to methods for evaluating the quality of clustering based on the extend to which documents associated with genes in a cluster collectively distinguish that cluster from all the other clusters, as well as the extent to which some words and phrases, present in documents associated with genes in the cluster, collectively distinguish that cluster from all the other clusters.

1 Claim, 1 Drawing Sheet

OTHER PUBLICATIONS

Tamayo, P., D. Slonim, J. Mesirov, Q. Zhu, S. Kitareewan, E. Dmitrovsky, E.S. Lander, and T.R. Golub. Interpreting patterns of gene expression with self-organizing maps: methods and application to hematopoietic differentiation. Proc Natl Acad Sci USA 96: 2907-2912 (1999).

Ben-Dor, A., R. Shamir and Z. Yakhini. Clustering gene expression patterns. J. Computational Biology 6:281-297 (1999).

Getz, G., E. Levine, E. Domany, and M.Q. Zhang. Super-paramagnetic clustering of yeast gene expression profiles. arXiv:physics/9911038 at preprint server xxx.lanl.gov (1999).

Perou, C.M., S.S. Jeffrey, M. van de Rijn, C.A. Rees, M.B. Eisen, D.T. Ross, A. Pergamenschikov, C.F. Williams, S.X. Zhu, D. et al. Distinctive gene expression patterns in human mammary epithelial cells and breast cancers. Proc Natl Acad Sci USA 96: 9212-9217 (1999).

Tibshirani, R., T. Hastie, M. Eisen, D. Ross, D. Botstein, and P. Brown. Clustering methods for the analysis of DNA microarray data. Manuscript from Web site http://www-stat.stanford.edu/~tibs/lab/publications.html (1999).

Kaufman, L. and P.J. Rousseeuw. Finding Groups in Data: An Introduction to Cluster Analysis. New York: Wiley (1990).

Holmes, I. and W.J. Bruno. Finding regulatory elements using joint likelihoods for sequence and expression profile data. Proc. Eighth International Conference on Intelligent Systems for Molecular Biology, AAAI Press, Menlo Park CA, pp. 202-210. (2000).

Yeung, K.Y., D.R. Haynor and W.L. Ruzzo. Validating clustering for gene expression data. Technical report UW-CSE-00-01-01. University of Washington, Seattle. Manuscript from Web site http://www.cs.washington.edu/homes/kayee/research.html (2000).

Shatkay, H., S. Edwards, W.J. Wilbur, and M. Boguski. Genes, themes, and microarrays. Using information retrieval for large-scale gene analysis. Proc. Eighth International Conference on Intelligent Systems for Molecular Biology, AAAI Press, Menlo Park CA, pp. 317-328. (2000).

Masys, D.R., J.B. Welsh, J.L. Fink, M. Gribskov, I. Klacansky, and J. Corbeil. Use of keyword hierarchies to interpret gene expression patterns. Bioinformatics 17: 319-326 (2001).

Delorie, D.J. Guide: What is DJGPP? Web page from http://www.delorie.com//djgpp/doc/ug/intro/what-is-djpp.html (1997).

McCallum, A.K. Rainbow. Web page from http://www.cs.cmu.edu/~mccallum.bow (1998).

Press, W.H., S.A. Teukolsky, W.T. Vetterling, and B.P. Flannery. Numerical Recipes in C. The Art of Scientific Computing, Second. edn. New York: Cambridge University Press (1992).

Manning, C.D. and H. Schutze. Foundations of Statistical Natural Language Processing. Cambridge MA: The MIT Press (1999).

Mitchell, T. Machine Learning. New York: McGraw-Hill (1997).

Egghe, L. and R. Rousseau. Introduction to Informetrics. Quantitative Methods in Library, Documentation, and Information Science. Amsterdam: Elsevier Science Publishers (1990).

Sonnhammer, E.L.L., S.R. Eddy, and R. Durbin. Pfam: a comprehensive database of protein domain families based on seed alignments. PROTEINS 28: 405-420 (1997).

Tamames, J., C. Ouzounis, G. Casari, C. Sander, and A. Valencia. EUCLID: automatic clasification of proteins in functional classes by their database annotations. Bioinformatics 14: 542-543 (1998).

Andrade, M.A. and A. Valencia. Automatic extraction of keywords from scientific text: application to the knowledge domain of protein families. Bioinformatics 14: 600-607 (1998).

Chaussabel, D. and A. Sher. Mining microarray expression data by literature profiling Genome Biology 2002, 3(10):research0055.1-0055.16 (2002).

Butler, B.A. Sequence analysis using GCG, Chapter 4 (pp. 74-97) in A.D.Baxevanis and B.F.F. Ouellette, eds. Bioinformatics. A Practical Guide to the Analysis of Genes and Proteins. New York: Wiley Interscience, 1998.

\* cited by examiner

SYSTEM, METHODS, AND COMPUTER PROGRAM PRODUCT FOR ANALYZING MICROARRAY DATA

CROSS REFERENCE TO RELATED APPLICATIONS

This patent application claims the benefit of U.S. Provisional Application No. 60/227,421, filed Aug. 23, 2000, which is hereby incorporated by reference.

STATEMENT REGARDING FEDERALLY SPONSORED RESEARCH AND DEVELOPMENT

Not applicable.

REFERENCE TO SEQUENCE LISTING, A TABLE, OR A COMPUTER PROGRAM LISTING APPENDIX

A computer program listing, entitled "bow-19991122", is submitted as an appendix on a single compact disc (plus one duplicate of that compact disc). The computer program listing is hereby incorporated by reference. The bow-19991122 software code is freely available, public domain software, as follows:

It is released under the Library GNU Public License (LGPL). You are welcome to use the code under the terms of the license for research or commercial purposes, however please acknowledge its use with a citation:

McCallum, Andrew Kachites. "Bow: A toolkit for statistical language modeling, text retrieval, classification and clustering." http://www.cs.cmu.edu/~mccallum/bow. 1996. Application No. 09/934,156 Filing Date Aug. 21, 2001 Art Unit 2168 Clean copy of application (without claims), incorporating previous amendments, enclosed as a courtesy to the Examiner, Cheyne D. Ly, with reply of Dec. 18, 2006 to Office Action of Sep. 20, 2006.

The "bow-19991122" software toolkit was downloaded on Mar. 18, 2000 from the above-mentioned Web site in compressed form, then uncompressed and extracted (with the UNIX "tar" utility program). The toolkit is contained on the compact disc within the "bow-19991122" directory, which contains 109 files (total size 1,868,349 bytes) and two subdirectories. The subdirectories are "argp", containing 32 files (total size 274,860 bytes), and "bow", containing 17 files (total size 128,038 bytes). The names of the individual files within the main-directory and sub-directories of the toolkit, along with their size in bytes and dates of creation, are listed in the transmittal letter that accompanies the compact disc. The compact disc also contains a file entitled Rainbow.htm, which is a browser-readable tutorial describing a computer program within the software toolkit, "Rainbow". The program "Rainbow" serves as a front-end for the toolkit, through which the user may invoke operation of the functions of the "bow" software toolkit. That tutorial file was written by Andrew McCallum and was copied from the above-mentioned Web site, on Mar. 22, 2000. The Rainbow.htm tutorial is hereby incorporated by reference.

BACKGROUND

1. Field of the Invention

The present invention relates generally to the field of bioinformatics, and specifically to systems, methods, and computer program products that make use of digital signal processing, clustering of data, statistical natural language processing, and machine learning, for purposes of analyzing data acquired using DNA arrays that have been hybridized with cDNA probes.

2. Description of Prior Art

Disease processes, as well as physiological responses to agents such as drugs, are often investigated by measuring the amounts of different messenger RNA (mRNA) species in a tissue specimen or in a cultured cell population. The present invention is concerned with analyzing such data, in particular, data acquired through use of a recently developed tool known as microarrays [DUGGAN et al., Nature Genetics 21, Suppl. 1:10-14 (1999)].

Microarrays consist of hundreds or thousands of spots of different DNA sequences, corresponding to many different genes, arranged in a grid pattern on a glass substrate or nylon membrane. Complementary DNA (cDNA) prepared from the mRNA of a tissue specimen is hydribidized to the microarray, which is then detected by fluorescence or autoradiographic methods. The signal detected at each of the many spots on the microarray is then used as an indication of the relative amount of the corresponding mRNA species in the specimen. Microarray experiments are often performed to compare mRNA levels from tissues under two conditions (e.g., cancerous vs. normal cells; before vs. after administration of a drug), in which case, the ratio of estimated mRNA levels for each microarray spot under the two conditions is also ordinarily calculated. The construction or interpretation of such ratio estimates may benefit from the application of statistical corrections, especially when spot values are close to the threshold of measurement detectability [CHEN et al., U.S. Pat. No. 6,245,517 (2001); NEWTON et al. (1999) from the Web site having the following domain name—top level domain=edu, second level domain=wisc, third level domain=stat, fourth level domain=www, path=/~newton/papers/publications.]

Microarrays have also been used to monitor the time course of mRNA levels in a cell population that had been subjected to an intervention, such as a shift in serum concentration in the growth medium, which alters the concentration of hormones and other factors needed for cell growth [IYER et al. Science 283:83-87 (1999)]. Those microarray measurements are typically made from mRNA collected at short time intervals (on the order of several minutes) immediately after application of the intervention, and longer intervals thereafter (hours). cDNA prepared from each of these mRNA samples is ordinarily hybridized to a separate array. Ratios are then constructed for each time point, as mentioned above, by dividing the measurement at the time point by a measurement corresponding to time-zero. After inspecting the time course of estimated mRNA levels for all the genes on the arrays in those experiments, investigators noted that the mRNA levels for certain groups of genes tend to fluctuate up and down together. Subsequently, computer algorithms were used to group together sets of genes (known as "clusters", produced by a clustering algorithm) according to the similarity of the time-course of their estimated mRNA levels, making the groupings more objective and relieving investigators of the burden of grouping the genes by eye [EISEN et al., Proc. Natl. Acad. Sci. USA 95:14863-14868 (1998); TAVAZONE et al., Nature Genetics 22:281-285 (1999); TAMAYO et al. Proc. Natl. Acad. Sci. USA 96:2907-2912 (1999); BEN-DOR et al. J. Computational Biol. 6:281-297 (1999); GETZ et al. (1999), arXiv:physcis/9911038 from the Web site having the following domain name—top level domain=gov, second level domain=lanl, third level domain=xxx; ZHENG et al., U.S. Pat. No. 6,263,287 (2001)].

Microarrays have also been used to measure cell responses to several different types of interventions, at a single time point, rather than the response to a single intervention at a series of time points. In those experiments, groups of genes were also observed to exhibit similar mRNA levels in response to the various interventions, and groupings of those genes were also produced automatically by using clustering algorithms [PEROUS et al., Proc. Natl. Acad. Sci. USA 96:9212-9217 (1999); TIBSHIRANI et al. (1999) from the Web site having the following domain name—top level domain=edu, second level domain=stanford, third level domain=www.-sta, path=/~tibs/lab/publications.html].

The similarity of estimated mRNA levels—observed among genes in individual clusters—could in some instances be coincidental, but most investigators attribute the similarity of mRNA levels to unknown biological control mechanisms, whereby functionally related genes are transcribed in a coordinated fashion in order to participate stoichiometrically in a biochemical or cell-physiological process. Thus, the clustering of genes on the basis of the similarity of their mRNA levels is viewed by investigators as an initial step in identifying functionally significant biochemical pathways or cell-physiological processes and their mechanisms of transcriptional control. For example, genes involved in mediating progression through the cell cycle may be found in the same cluster [IYER et al., supra]. However, it has also been observed that genes with supposedly similar known functions do not always appear together in the same clusters [TAVAZOIE et al., supra]. This may be due in part to inadequacy of the particular clustering algorithm that was used. If a different clustering algorithm were applied to the data, it would generally produce different clusters and may be more successful at grouping together functionally related genes.

Initially, investigators applied hierarchical clustering algorithms to array data [EISEN et al., supra]. Later investigators used self-organizing maps, to perform clustering [TAMAYO et al., supra]. Other investigators have performed clustering of microarray data using the k-means algorithm [TAVAZOIE et al., supra], a graph theoretical algorithm [BEN-DOR et al., supra], super-parametric clustering [GETZ et al., supra], as well as grid and σ-τ clustering [ZHENG et al., supra]. Variations of these algorithms have also been implemented by using various normalizations and distance measures. Additional clustering algorithms were described for situations in which data are parameterized by two or more variables [TIBSHIRANI et al., supra]. Considering that hundreds of other general-purpose clustering algorithms have been described [KAUFMAN and ROUSSEEUW. Finding Groups in Data: An Introduction to Cluster Analysis, Wiley (1990) and references contained therein; MANNING et al., Chapter 14, "Clustering", in Foundations of Statistical Natural Language Processing, MIT Press (1999)], many of which may eventually be applied to microarray data, and considering that all of these clustering algorithms may group microarray data in different ways, investigators have the problem of deciding which of those algorithms is most useful for analyzing their data.

the inability to group functionally related genes into individual clusters may also be due to factors other than the use of a sub-optimal general-purpose clustering algorithm, for the following reason. It is thought that the similarity of mRNA levels for the various genes in each cluster may be due to co-regulation of those genes by shared transcription factors. In fact, some investigators use an algorithm that simultaneously clusters genes on the basis of the similarity of their estimated mRNA levels, as well as whether those genes exhibit shared DNA binding sites to which the transcription factors can bind [HOLMES et al., Proc. Int. Conf. on Intelligent Systems for Molecular Biology 8:202-210 (2000)].

When clustering is to be performed, one therefore needs to compare results made with different clustering algorithms, in order to decide which algorithm is most useful for the data under investigation. The comparison may be made first in terms of the statistics of how well members of each cluster resemble their corresponding centroid (i.e., tightness of clustering), or in terms of a figure of merit obtained using a resampling approach [YEUNG et al. (2000) from the Web site having the following domain name—top level domain=edu, second level domain=washington, third level domain=cs, fourth level domain=www, path=/homes/kayee/research.html]. However, such goodness-of-fit comparisons do not assess the quality of clustering in terms of the biological reasonableness of the results, which must be based on the physiological functions of the genes in the clusters.

However, there is little prior art that can assist investigators in evaluating the extent to which genes in clusters are functionally related, which has been taken to be a primary criterion upon which the quality of clustering is judged. The main difficulty in establishing functional relations among genes in clusters lies in the unavailability or incompleteness of factual databases that explicitly link the known functions of genes with one another. TAVAZOIE et al., supra, indexed yeast genes using the 199 functional categories in the Martinsreid Institute of Sciences functional classification scheme database (ribosomal, mitochondrial, TCA pathway, etc.). For each cluster of genes, they then calculated probabilities (P values) of the frequency of observed genes in the various functional categories, to determine whether particular clusters are significantly composed of genes associated with particular functional categories. However, such functional classification databases are available to characterize the genes of only a limited number of organisms, or they may not contain a complete list of known genes. Furthermore, those databases force genes into a predetermined classification scheme that may contain overly-broad or overly-narrow classifications, or classifications that are not mutually exclusive. Possibly for this reason, TAVAZOIE et al. supra, found that genes with supposedly similar known functions—as defined by the Martinsreid Institute of Sciences functional classification scheme database for yeast—do not preferentially appear together in the same cluster.

Consequently, most investigators simply review the lists of clustered genes manually and then offer expert commentary about the functional significance of genes of the various clusters, based on their reading of the literature about those genes. For example, IYER et al., supra, describe one cluster as being enriched for genes "involved in mediating progression through the cell cycle", describe another cluster as containing genes encoding "proteins involved in cellular signaling", and for other clusters they offer no description. At the present state of the art, expert human judgement may well be the best method for evaluating the relatedness of functions of genes in clusters. However, this method is limited by the expertise of its practitioners, as well as by the considerable labor involved in manually reviewing literature concerning the many genes that may be present in the clusters. In fact, even the task of identifying the relevant articles in the scientific literature is arduous.

In the invention, text in the scientific literature is obtained about genes on a microarray (using an original method that is part of the invention), by putting that literature in groups defined by microarray clustering of the corresponding genes; and by then constructing a mathematical model of the text. The purpose of the model is to identify words or phrases that are most uniquely associated with the text corresponding to each cluster, and that also best distinguish each cluster from the others.

An advantage of the present method and system is that it does not presuppose the existence of a structured database of gene annotations, such as the Martinsreid Institute of Sciences functional classification scheme database for yeast, which was mentioned above. A further advantage of the present system is that it automatically generates a list of words or phrases ("annotations") that best describe each cluster and that also best distinguish each cluster from the others. The present method and system produces those words and phrases in a different manner that what was outlined by SHATKAY et al., Internat. Conf. on Intelligent Systems in Molecular Biology 8:317-323 (2000). Unlike the present invention, their method does not make use of information from the clustering of microarray data. Furthermore, they use a semi-automatic—rather than automatic—method that attempts to find literature citations and keywords that are conceptually related to single documents, which must be specified by the user for each gene.

The present method and system also produces words and phrases in a different manner than what was described by MASYS et al., Bioinformatics 17:319-326 (2001). Their method has the disadvantage that the words and phrases it produces are voluminous and generally non-specific, placing a significant burden of interpretation on the investigator, because it links sets of genes to the published literature by way of keyword hierarchies using the entire set of descriptors contained in MeSH and Enzyme Commission nonmenclature.

BRIEF SUMMARY OF THE INVENTION

A system and methods for analyzing microarray data includes a computer having a central processing unit and a computer memory, which are used to run computer program modules. The computer program modules, along with experimental signal data representing relative concentrations of particular mRNA species (indexed as nucleic acid accession numbers), are loaded initially into the computer memory from a computer disk. One computer program module groups the mRNA species (or nucleic acid accession numbers) into clusters, each cluster being a subset of the mRNA species (or of the corresponding nucleic acid accession numbers). Other computer program modules associate multiple unique identifiers, corresponding to scientific publications describing gene structure and functions, with each of the genes in each of the clusters.

In one embodiment of the invention, a computer program module obtains literature abstracts and other text corresponding to the above-mentioned literature unique identifiers. A computer module organizes that text in computer files according to the clustering of the corresponding genes, then constructs a mathematical model of the text. The purpose of the model is to identify words or phrases in the text that are most uniquely associated with the text corresponding to each cluster, and that also best distinguish each cluster from the others. Thus, the method and system automatically generate words and phrases that characterize the functional or structural or interactional relations among genes within the clusters. Output data are accumulated and presented concerning the above-mentioned clusters, words and phrases.

OBJECTS AND ADVANTAGES

Objects and advantages of the present invention include the following:

A further advantage of the invention is that it generates, in a totally automatic manner, a list of key words or terms that not only characterize each cluster but that also distinguish each cluster form all the other clusters.

A yet further advantage of the invention is that it provides an automatic method for identifying the relevant literature.

DETAILED DESCRIPTION OF THE PREFERRED EMBODIMENTS

Figure 1:
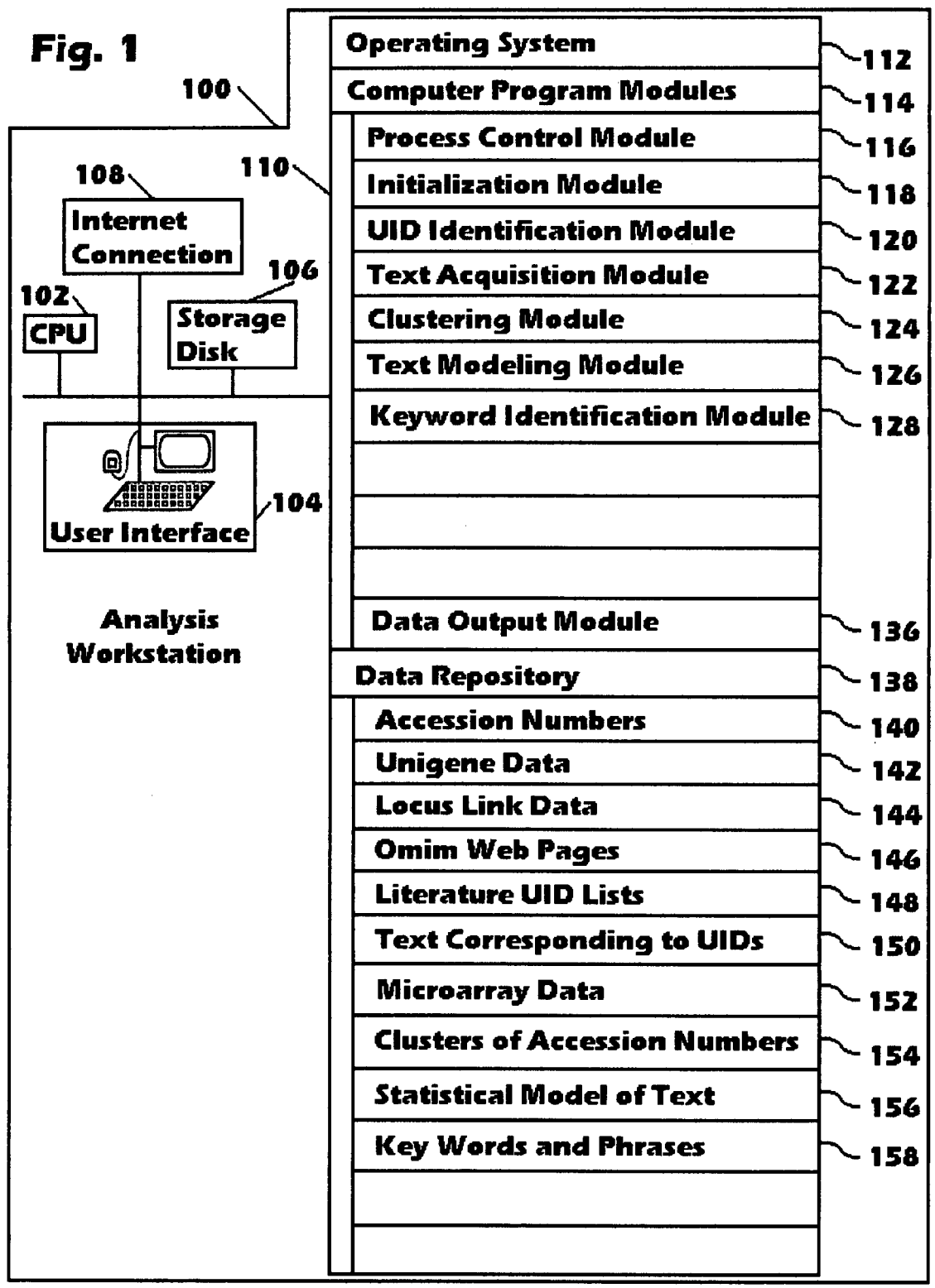
FIG. 1 is a block diagram of a preferred embodiment of the system and computer program product for analyzing microarray data.

The present invention is not limited to any particular hardware or operating system environment. Those skilled in the art will understand that the systems and methods may be implemented using a variety of computer platforms, operating systems, and programming languages. Therefore, the following description of specific embodiments of the present invention is for purposes of illustration only.

Hardware

The device for analyzing microarray data is shown in FIG. 1. It consists of a computer workstation (100), which has Pentium III central processor unit, abbreviated as CPU (102), and which is connected to the Internet using a cable modem and a 10/100 network interface card (108). The workstation's User Interface (104) makes use of a monitor, keyboard, and mouse. The workstation's operating system, computer program modules, and data repository are loaded into a 512 Megabyte computer memory (110) from files on a 34 Gigabyte hard storage disk (106).

Operating System

The operating system for the workstation (112) is Microsoft Windows 98, augmented with additional software that allows operation of the workstation to resemble a UNIX system, namely, operate in the GNU software environment, which is described at the Web site having the following domain name—top level domain=org, second level domain=fsf, third level domain=www. This additional software is DJGPP version 2.03 [Delorie (1997)], obtained over the Internet at the ftp site having the following domain name—top level domain=net, second level domain=simtel, third level domain=ftp, path=/pub/simtelnet/gnu/djgpp. The workstation's augmented operating system contains all the utility programs that are customarily downloaded for installation with DJGPP, such as perl, flex, bash, grep, and GNU Fileutils.

Installation of DJGPP is necessary in order to install the text modeling program module (126), keyword identification module (128), and associated text classification software. These modules make use of the "bow" software toolkit for statistical language modeling, text retrieval, classification, and clustering (version 1999.11.22), which is submitted as an appendix "bow-19991122" on a compact disc, in particular, its open source code. Installation of the "bow" software toolkit was performed as described in the instructions that come with the toolkit, except that the system utility program "autoconf" was run to produce a new "configure" file, instead of using the "configure" file that come with the distributed "bow" software.

Computer Program Product

The computer program modules (114) are loaded from the computer storage disk (106) into the computer memory (110) in order to perform individual tasks in the analysis of microarray data. Because some Users may already have the hardware and operating system software of the system, which are described above, the computer program modules (114) along with the associated data repository (138) by themselves constitute a computer program product, which such Users would then install on their available computers.

Process Control and Specifying Options

The analysis process is initiated by the User at the User Interface (104), for example, by typing the name of the Process Control Module (116) at a DOS prompt, which causes the operating system to load and run the Process Control Module (116). At the time of initiation the User may also specify analysis options, for example in an "argv[]" command line format that is used for computer programs written in the C Language. The options instruct the Process Control Module to proceed in a manner other than by using default parameters of the analysis process. These options are stored for subsequent use as the values of variables within the Process Control Module.

The Process Control Module, in turn, loads and runs other modules, many of which could actually be run independently by the user. For example, the User could type the following MS-DOS or bash command line to cause a computer program called "rainbow" to perform text classification of text files located in subdirectories of a directory called "clusters_text", and then place the results of the classification in a directory called "text_model" (as described in documentation at the Web site for the "bow" software, [McCALLUM (1998)], from the Web site having the following domain name—top level domain=edu, second level domain=cmu, third level domain=cs, fourth level domain=www, path=/~mccallum/bow):

```
rainbow-d.\text_model—index.\ clusters_text\*
```

However, the Process Control Module (116) does the same thing automatically as one of the steps in the overall analysis process, by running the Text Modeling Module (126) that in turn runs the "rainbow" program. The program line within the Text Modeling Module (126) that does so, written in the program language C, is as follows:

```
system("rainbow -d.\ \ text_model—index.\ \ clus-
    ters_ text\ \*"");
```

It is well known by computer programmers that the same type of process control can also be accomplished by using a shell script, or by jumping directly to computer memory locations corresponding to compiled libraries or subroutines, rather than by invoking such a system(". . . ") function within a compiled computer program.

Glossary

Description of the method used in the workstation system (100) to analyze microarray data follows. In order to assist the reader to understand the description, the following glossary of terms is first provided.

Accession number or gene accession number: A researchers who sequences some DNA often deposits that sequence information into a public DNA sequence database, such as GenBank. When the curators of the DNA sequence database enter that sequence information into the database, they assign a unique, permanent identifier to the sequence, which is known as the sequence's accession number. It consists of a alpha-numeric string, such as "W95909". DNA in each spot on the microarray has been sequenced (in whole or in part), and that sequence may be ascertained from a database like GenBank by specifying the known accession number corresponding to that spot.

UniGene Number: Many of the DNA sequences that have been assigned accession numbers are similar to the sequences corresponding to other accession numbers, because different researchers may have sequenced the same gene and deposited the sequence information independently. UniGene is a database that groups together different accession numbers corresponding to similar sequences. Each such grouping of accession numbers is assigned a number (UniGene number). Thus, the accession numbers that have been assigned a particular UniGene number have DNA sequences that are similar to one another.

LocusLink Number: The Locus Link database groups together entries from several databases that involve not only DNA sequence information (such as UniGene data), but also such things as the chromosomal location of the DNA sequence, the Enzyme Commission number of the corresponding protein (if it is an enzyme), and the diseases with which the corresponding gene are associated (if known). Each grouping of database entries about a particular gene is assigned a number (Locus Link number).

Omim Number: Omim is an abbreviation for "Online Mendelian Inheritance in Man", which is a database that describes the connection between particular genes and diseases. Each gene in the Omim database is assigned an identifying number (Omim number). The Locus Link database entries include the Omim number if it exists. There is a Web page for each of the genes in the Omim database, which contains links to relevant scientific literature about the corresponding gene.

UID or PubMed UID: PubMed is a database of biomedical scientific publications. Every scientific article from the journals that are indexed by PubMed is identified by a unique, permanent number—the Unique IDentifier number ("UID" or "uid").

rainbow: This is the name of a computer program written by McCallum and colleagues at Carnegie Mellon University. It may be used to classify text files. Given examples of text files that deal with a specified number of different subjects (classes), it first examines the text in those files to determine the vocabulary that distinguishes the different subjects (classes). Then, given a text file on an unknown subject, it classifies that file as pertaining most closely to one of the different known subjects, based on the vocabulary that it contains.

Process of Analyzing Microarray Data

The Process Control Module (116) begins the analysis by initiating tasks that are to be accomplished by the Initialization Module (118). The first such task is to read a file of gene accession numbers, corresponding to the DNA species that have been spotted onto the microarray under investigation, for which partial sequences are known. The list of accession numbers are stored for future use in the Data Repository (138), in the section Accession Numbers (140).

The next task of the Initialization Module (118) is to associate each of the accession numbers with a gene that has been characterized (if possible). It does so by first converting accession numbers to UniGene numbers. It then converts UniGene numbers to LocusLink numbers. Finally, it converts LocusLink numbers to Omim numbers. Each of these conversions is accomplished by using look-up table data, in which the associations between the labelings of different types of data are listed explicitly. These steps are described in more detail in the paragraphs that follow.

The data pointing from accession numbers to UniGene numbers are ready by the Initialization Module (118) from a file on the storage disk (106) and stored in the Data Repository in the section UniGene Data (142). The data in that file are obtained for each new build of UniGene by downloading the file Hs.data.Z (for human genes) from the Web site having the following domain name—top level domain=gov, second level domain=nih, third level domain=nlm, fourth level domain=ncbi, fifth level domain=ftp, path=/pub/schuler/Unigene, then extracting the accession-to-unigene number data and formatting the data for storage on the disk (106). The extraction consists of uncompressing the compressed file to become Hs.data, then scanning the resulting text file for lines containing ID Hs. "u" followed by SEQUENCE ACC="a", where "u" is a UniGene number and "a" is a corresponding accession number.

The procedure described above pertains to microarray data concerning human DNA. For non-human species (e.g., mouse and rat), the "Hs" in the paragraph above is replaced by the symbol for each of the corresponding species. If the microarray data under analysis are non-human, an additional step is performed to convert the non-human indices to those for the homologous human genes. This extra step consists of using a look-up table to link the UniGene number for the non-human gene with the homologous human UniGene number. The file hmlg.ftp, downloaded from the Web site having the following domain name—top level domain=gov, second level domain =nih, third level domain=nlm, fourth level domain=ncbi, fifth level domain=ftp, path=/pub/Homologene, and stored on the workstation's disk (106), contains that look-up table data. It is read by the Initialization Module (118), which stores the data in the UniGene Data section (142) of the Data Respository (138).

The data pointing from UniGene to LocusLink numbers are also read by the Initialization Module (118) from a file on the storage disk (106) and stored in the Data Respository in the section LocusLink Data (144). The data in that file had also been extracted from the file Hs.data. The extraction consists of scanning the text file for lines containing ID Hs. "u" followed by LOCUSLINK "L", where "u" is a UniGene number and "L" is the corresponding LocusLink number.

The data pointing from LocusLink To Omim numbers are also read by the Initialization Module (118) from a file on the storage disk (106) and stored in the Data Respository in the section LocusLink Data (144). The data in that file had been extracted from the file LL_templ, downloaded from the Web site having the following domain name—top level domain=gov, second level domain=nih, third level domain =nlm, fourth level domain=ncbi, fifth level domain=ftp, path=/refseq/LocusLink. The extraction consists of scanning the text file for lines containing >>"L" followed by OMIM: "o", where "L" is the LocusLink number and "o" is the corresponding Omim number.

The Initialization Module (118) then links the Accession Numbers in (140) to Omim numbers by following the pointers to UniGene numbers, then to LocusLink numbers, then to Omim numbers. Sometimes, no Omim number can be associated with an accession number because the corresponding pointers do not exist. In that case, the accession number is associated with a number (zero), indicating that no corresponding Omim number could be found. Sometimes, more than one Omim number can be associated with an accession number, for example, because the LocusLink table links a UniGene number with more than one LocusLink number. In that case, all of the corresponding Omim numbers are placed in the table associated with that accession number entry, which is stored in the LocusLink Data section (144) in the Data Repository (138).

Upon completion of these steps by the Initialization Module (118), the Process Control Module (116) initiates operation of the UID identification module (120). Its function is to construct lists of literature Unique IDentifier ("UID" or "uid") numbers, which uniquely identify publications in the scientific literature that describe the genes associated with the accession numbers of the microarray spots. The UID identification module constructs those lists by first downloading Web pages associated with the Omim numbers, those numbers having been obtained as described in the previous paragraph. The UID Identification module (120) then scans the Omim Web pages for UID numbers, creating lists of UIDs that are associated with the microarray spots that had been linked to the Omim numbers. These steps are now described in more detail.

Specifically, for each Omim numbers stored in the LocusLink Data section (144) of the Data Repository (138), the UID identification module (120) constructs a Web URL address of the form "http://" followed by a domain name of the following form—top level domain=gov, second level domain=nih, third level domain=nlm, fourth level domain=ncbi, fifth level domain=www, path?query=/htbin—post/Omim/dispmin?"Omimnumber", where "Omimnumber" is one of the Omim numbers mentioned above.

The UID identification module (120) then requests this Web page by placing the Web address onto the Internet over the Internet Connection (108) and waits for a reply. It stores the reply on the disk (106), saving it as hypertext markup language text with the name "Omimnumber.html".

After downloading all of the Omim Web page files corresponding to the Omim numbers that had been associated with spots on the microarray, the UID Identification module (120) extracts literature Unique IDentifier ("UID") numbers from these Web page files. It does so by scanning lines in each of the files for text of the form "db=m&form=6&dopt=d&uid=n1, n2, . . . ", where the integers n1, n2, . . . are a sequence of UID numbers separated by commas. The "db=m" indicates that the UID numbers that follow are from the MedLine literature database. Then, the UID Identification module (120) extracts from the strings the numbers n1, n2, . . . , which are separated by commas, which are bounded on the left by "&uid=", and which are bounded on the right by a character other than a comma or numeral 0 to 9. After all such UID numbers have been extracted from the Omim Web page, any repeated UID numbers are eliminated. In this preferred embodiment, this is done by sorting the numbers in ascending order using a standard sorting algorithm [Press et al (1992)], then examining them sequentially, removing an entry if it has the same value as the one that was examined previously. The sorted, non-duplicate UID numbers are then stored by the UID Identification Module (120), along with their corresponding Omim number in the section Literature UID Lists (148) of the Data Respository (138).

Upon completion of these steps by the UID Identification Module (120), the Process Control Module (116) initiates operation of the Text Acquisition Module (122). Its function is to download over the Internet and filter the text files that are to be used to characterize the microarray data. When acquiring and filtering these data, the Text Acquisition Module (122) stores text data temporarily in the section Text Corresponding to UIDs (150) in the Data Respository (138). For each UID corresponding to each Omim number, obtained from the section Literature UID Lists (148) of the Data Repository (138), the UID Identification Module (12) constructs a Web URL address of the form "http://" followed by a domain name of the following form—top level domain=gov, second level domain=nih, third level domain=nlm, fourth level domain=ncbi, fifth level domain=www, parh?query=/htbin—post/Entrez/query?db=m&form=6&dopt=1&html=no&uid=UID, where "UID" is one of the UID numbers.

This Web URL address represents a query to obtain the literature citation, abstract, and indexing terms corresponding to the indicated UID number. The requested output format is MEDLARS, with hypertext formatting removed. Since March 2000, the base URL may also correspond to a Web site having the following domain name—top level domain=gov, second level doamin=nih, third level domain=nlm, fourth level domain=ncbi, fifth level domain=www, path=/entrez/utils/qmap.cgi. (See Web address having the following domain name—top level domain=gov, second level domain=nih, third level domain=nlm, fourth level domain=ncbi, fifth level domain=www, path=/entrez/utils/qmap_help.html, for alternate ways to construct the URL). The Text Acquisition Module (122) then requests this Web page by placing the Web URL address onto the Internet over the Internet Connection (108) and waits for a reply. It stores the reply on the disk (106), appending it to a text file having the name of the Omim number with which the UID is associated ("Omimnumber.txt"), with a delimiter line (like ">>UID Uidnumber") written to separate successive UID downloads for that Omim number. All such files are stored by default in a specific directory (\Omim).

When all of the text corresponding to all of the UID numbers for all of the Omim numbers has already been downloaded, the User may also specify as an option that the system use those files for analysis, rather than download them all again. The Text Acquisition Module (122) may then also filter the text files, depending on the options that had been specified by the User at the User Interface (104). The options are to filter out specific categories of text that are contained in the MEDLARS formatted Web pages. The categories of text are delimited in the files by labels such as AB—(for abstract), TI—(for the title of the literature citation), and MH—(for an index term characterizing the subject of the article), any or all of which can be retained as an option. For example, for the option of analyzing only the literature abstracts, the Text Acquisition Module (122) will scan the text files until the delimiter "AB—" is found and copy the subsequent text to another file containing the filtered text, until another delimiter is found. It then stops copying to the second file until another "AB—" is encountered. The latter file has the same name as the original file, plus an extension like ".AB" appended to the file name, indicating that it contains only the "abstract" category of text. Delimiter lines associating the filtered text with their UID numbers may also be retained as an option.

Clustering of Microarray Data

Upon completion of these steps by the Text Acquisition Module (122), the Process Control Module (116) initiates operation of the Clustering Module (124). Its function is to organize the accession numbers (and therefore the associated UniGene numbers, LocusLink numbers, Omim numbers, and UID numbers and associated text files) into separate groups, known as clusters. The clusters are numbered 1, 2, 3, . . . up to some maximum cluster number (Cmax).

If the clustering has already been performed external to the Computer Program Modules (114), the User must have specified at the User Interface (104) the option of using externally clustered data. In that case, the Clustering Module (124) reads the name of the file that contains the clustering data (specified in the option by the User), then reads that file and places the data it contains in the section Clusters of Accession Numbers (154) in the Data Respository (138). That data consists of the number of clusters (Cmax), as well as the accession numbers contained in each of the Cmax clusters. In principle, the same accession number could be found in more than one cluster, but most clustering algorithms place each accession number in only one cluster. In the event that some of the accession numbers in the section Accession Numbers (140) of the Data Respository (138) are not present in any of the Cmax clusters, they are placed in a cluster of previously ungrouped accession numbers, which is defined to be cluster number "zero".

If the microarray data have not already been clustered externally, the Clustering Module (124) performs the clustering itself. The clustering is performed using mircoarray data that must be provided in a file that had been specified by the User at the User Interface (104). The microarray data are in the form of a spreadsheet table, in which each row corresponds to the respective accession numbers in the Accession Number section (140) of the Data Repository (138), and the columns correspond to different experimental conditions (e.g., response to different interventions, each measured at a single time point; OR response to a single intervention at an initial time, measured at different subsequent times). The entry in each cell of the table is an integrated spot intensity (normalised so that reference spots have the same values for all conditions, and with unwanted background subtracted), measured in fluorescence or radioactivity units, for the microarray spot associated with the row's accession number. Alternatively, the entry in each cell of the table may be a dimensionless ratio, in which the numerator is the integrated spot intensity for that particular condition or time point, and the denominator is the baseline integrated spot intensity (value in the absence of the intervention, or value at time zero). It is also assumed that any other statistical corrections, such as those described by NEWTON et al., supra, have already been applied, so that any errors introduced by the measurement process itself are largely eliminated. After the microarray data are read from the input file, they are stored in the Microarray Data section (152) of the Data Repository (138).

As an option, the User at the User interface (104) may instruct the Clustering Module (124) to add different amounts of noise to the microarray data described in the previous paragraph, in order to evaluate the robustness of the results that are eventually obtained without the addition of noise. The parameter of the option is the coefficient of variation of the statistical distribution that is sampled and added to the integrated spot intensity or ratio corresponding to each spot of the microarray. The statistical distribution is normal distribution with a mean equal to the given spot intensity and a standard deviation given by the mean times the coefficient of variation. Sampling of the statistical distribution makes use of standard random number generator methods [PRESS et al., Numerical Recipes in C, Cambridge Univ. Press (1992)]. Because the spot intensity is constrained to be a non-negative number, in the event that the sampled random number is negative, it is then set equal to zero.

Clustering of these data by the Clustering Module (124) is performed using the algorithms described in the section "Backgroun—Description of Prior Art." The default method is an adaptation of the k-means algorithm, as implemented in the computer program CLARA [KAUFMAN et al., supra], source code for which was downloaded from the Web site having the following domain name—top level domain =edu, second level domain=cmu, third level domain=stat, fourth level domain=lib, path/32 /general/clusfind.

When it was included in our system, CLARA was unchanged, except that we made it possible for CLARA to obtain parameter values for its algorithm from the Computer Program Modules (114), rather than by independently prompting the User. Thus, when using this default algortlm for clustering, the User may specify the parameters for the CLARA program as options at the system's User Interface (104), and the Clustering Module (124) subsequently runs the program CLARA using a system(". . . ") function, as described earlier. In particular, the User may select the number of clusters that are to be constructed (Cmax). After the clustering has been performed, the Clustering Module (124) stores results in the section Clusters of Accession Numbers (154) of the Data Repository (138), namely, the number of clusters (Cmax), as well as the accession numbers contained in each of the Cmax clusters.

Text Modeling

Upon completion of these steps by the Clustering Module (124), the Process Control Module (116) initiates operation of the Text Modeling Module (126). Its first function is to group the text associated with accession numbers—the text having been obtained with the TextAcquisition module (122)—so as to correspond to the clusters in the Data Repository section Clusters of Accession Numbers (154). It then produces a statistical model of the text that is suitable for text classification. The model contains, for example, the number of times that a term like "mitosis" appears in different documents. To do so, it first creates a directory called \ clusters_text, and within this directory it creates subdirectories \0, \1, \2, . . . , \Cmax corresponding to each of the clusters. For each of the accession numbers in data section Accession Numbers (140), it then copies files produced by the Text Acquisition Module (122) into the subdirectories, according to the cluster to which that accession number has been assigned by the Clustering Module (124). If an accession number could not be associated with a Omim number, or if that Omim number could not be associated with any UIDs, then the Text Modeling Module (126) proceeds to the next accession number without copying files. The Text Modeling Module (126) then performs the following system function (written in the C programming language):

system("rainbow -d.\ \ text_model—index .\ { clusters_text\ {*");

to instruct the computer program 'rainbow' to use the text found in subdirectories of the directory \ clusters_text, make a statistical model of the text, then store the results in a directory called \ text_model [McCALLUM, supra]. Results are also stored in the Data Repository (138) in the section Statistical Model of Text (156). When making the statistical model, the rainbow program turns the stream of characters in each file into words called "tokens". By default, all sequences of characters are converted to lowercase (e.g., "A" becomes "a") to form the tokens, and any token that is in a stoplist of common words (e.g., "the", "of", "is") are ignored. The model that is then formed constitutes a sparse matrix of the number of times that each of the tokens is found in each of the text files in each of the subdirectories. Many options for the rainbow computer program may also have been specified by the User at the User Interface (104), which are subsequently passed to the rainbow computer program by the Text Modeling Module (126) using a system (". . . ") function. The possible options are listed in the documentation for the 'rainbow' computer program, which is submitted in an appendix on a compact disc as "Rainbow.htm", as well as its "rainbow—help" on-line documentation.

Three examples of those options are as follows. (1) Pass the words of the files through a stemmer (e.g., change "experimenting" to "experiment"). (2) Create N-gram tokens (e.g., with a bi-gram, "cell cycle" is used as a token, not just individual words, "cell" and "cycle"). (3) Prune the word list by ignoring words that occur less than some specified number of times in the text files.

Once the text has been modeled by the Text Modeling Module (126), the Process Control Module (116) initiates operation of the Keyword Identification Module (128), which uses the rainbow computer program to acquire various diagnostic information about the model. The information that is provided automatically by the Keyword Identification Module (128) is a list of words for each cluster, sorted in descending order according to the numerical weights calculated by a classification algorithm. The default method that the program rainbow uses for classification is the Naive Bayes method, otherwise known as Evidence Classification or simply the Bayes method. This method, along with applications related to text classification, is explained in Chapter 6 or MITCHELL, Machine Learning, McGraw-Hill (1997). The User at the User Interface (106) may also specify as an option that a different method be used by the computer program 'rainbow' to perform the classification, including support vector machines (svm), term frequency-inverse document frequency (tfidf), probabilistic indexing (prind), maximum entropy (maxent), k-nearest neighbors (knn), EM algorithm (em), Dirichilet kernel (dirk), and Active Learning (active). These options are then requested by the Text Modeling Module (126) by issuing a system(". . . —method—METHOD . . . ")

command for the indicated options to be performed by the rainbow computer program, where METHOD is one of the methods indicated above in parentheses.

The following system function, written in the C programming language, is used by the Keyword Identification Module (128) to generate the word lists:

system("rainbow -d.\ \text_model—print-word-weights=cluster_name>word-weights_cluster_anme.txt");

where cluster_name is the name of a cluster (0,1,2, ... or Cmax) and where word-weights_cluster_name.txt is the name of a text file that is to contain the words and corresponding weights for that particular cluster. Word lists for each of the clusters are generated in succession by performing a system command of this form, but with different cluster names (i.e., cluster numbers). The results are stored on the storage disk (106) in the indicated word-weight file, the contents of which are read into the section Key Words or Phrases (158) in the Data Repository (138) by the Keyword Identification Module (128). By default, only words with positive weights are read into the Key Words or Phrases section (158), sorted in descending order according to the weight values. As an option, words with negative word weights may be included as well. Examples of such word lists are given in Tables 1 and '.

Additional word-list diagnostic information may be requested as an option by the User at the User Interface (104). Those options [McCALLUM, supra] are available through the rainbow computer program, for example, a list of words that have the highest log odds ratio score for each cluster. The default number of words is 20 per cluster, obtained by the following system function in the C programming language: system("rainbow -d.\ \ text_model—print-log-odds-ration=20>log_odds_word_list.txt"); The results are stored on the storage disk (106) in the file log_odds_word_list.txt, the contents of which are read into the section Key Words or Phrases (158) in the Data Repository (138) by the Keyword Identification Module (128). Another example of a word list option is a list of words having the highest mutual information with the cluster index, sorted by the magnitude of the mutual information. A description of such options is present in the on-line documentation for the rainbow program.

The Process Control Module (116) initiates operation of the Data Output Module (136). It displays the key words or phrases.

EXAMPLES USING THE PREFERRED EMBODIMENTS

The examples make use of microarray data that are described in IYER et al., supra, which are available at the Web site having the following domain name—top level domain=edu, second level domain=stanford, third level domain=genome-www.

They are from an experiment in which quiescent human diploid fibroblasts were stimulated to proliferate by increasing the concentration of fetal bovine serum in their growth medium. At 12 time points after addition of the serum, samples of mRNA were collected and used to prepare cDNA for hybridizing to an array. Five hundred-seventeen genes on the array were observed to show significant up- or down-regulation, as defined in IYER et al., supra. The microarray data corresponding to these 517 genes were clustered using a hierarchical clustering algorithm [EISEN et al., supra], resulting in 10 clusters, labeled A through J in FIG. 2 of IYER et al., supra. Accession numbers for all the genes represented as spots on the microarray are available at the Web site given above.

Analysis of these data made use of information extracted from Build 96 of the Unigene database, which was contained in the file Hs.data.Z, downloaded from the Web site having the following domain name—top level domain=gov, second level domain=nih, third level domain=nlm, fourth level domain=ncbi, fifth level domain =ftp, path=/pub/schuler/Unigene The analysis also made use of information extracted from the Locus Link database (version Sep. 10, 1999), which was downloaded as the file LL_templ at the Web site having the following domain name—top level domain=gov, second level domain=nih, third level domain=nlm, fourth level domain=ncbi, fifth level domain =ftp, path=/refseq/LocusLink.

Processing of these data to associated the accession numbers with Omim numbers proceeded as described in the Preferred Embodiment, through points from accession numbers to UniGene numbers to LocusLink numbers to Omim numbers. Among the 517 accession numbers in the test data, 237 of them could be associated with Omim numbers. Most of the others were unidentified ESTs, which were excluded from further analysis by associating them with Omim number "0".

The UID Identification Module (120) in FIG. 1 then downloaded Omim Web pages corresponding to those Omim numbers and extracted from them Unique IDentifier numbers ("uids"), as described in the Preferred Embodiment. A total of 19,643 uids were associated with 237 Omim numbers.

The Text Acquisition Module (122) in FIG. 1 then downloaded text files corresponding to these 19,643 uids, storing them in 237 files having the names of the corresponding Omim numbers, as described in the Preferred Embodiment.

The Clustering Module (124) in FIG. 1 then clustered the 517 accession numbers using an externally available clustering scheme, which is the one shown in FIG. 2 of IYER et al., supra. The clusters, associated with the acession numbers of the clustered genes, were obtained at the Web site having the following domain name—top level domain=edu, second level domain=stanford, third level domain=genome-www. For use in the example, the clusters that IYER et al., supra, had labeled A through J were relabeled 1 through 10, and accession numbers that had not been associated with a cluster were put into a cluster "zero".

The Text Modeling Module (126) processed the text associated with the accession numbers of the examples, as described in the Preferred Embodiment section, followed by processing the Keyword Identification Module (128). For the data clustered externally as given in IYER et al., supra, examples of the list of Keywords characterizing the clusters are shown in Tables 1 and 2. Table 1 gives keywords for Cluster D, and Table 2 gives keyword for Cluster B.

TABLE 1

| TOP 25 KEYWORDS FOR CLUSTER D. | |
|---|---|
| WEIGHTS | KEYWORDS |
| 0.012058684 | msh |
| 0.007730326 | hnpcc |
| 0.004746247 | mismatch |
| 0.004467339 | colorectal |
| 0.004294871 | arf |
| 0.002764531 | hmsh |
| 0.002495748 | crm |
| 0.002355605 | kinetochore |
| 0.002203363 | mlh |
| 0.002048244 | ebna |
| 0.001990554 | nonpolyposis |
| 0.001818067 | hmlh |
| 0.001784532 | export |
| 0.001580882 | nes |
| 0.001388732 | mmr |
| 0.001341535 | msi |

TABLE 1-continued

TOP 25 KEYWORDS FOR CLUSTER D.

| WEIGHTS | KEYWORDS |
| --- | --- |
| 0.001280268 | topoisomerase |
| 0.00124356 | spindle |
| 0.001199594 | ebv |
| 0.001149875 | primase |
| 0.001112527 | repair |
| 0.001073333 | kinetochores |
| 0.001050086 | mad |
| 0.001013135 | replication |
| 0.000948283 | muts |

TABLE 2

TOP 25 KEYWORDS FOR CLUSTER B.

| WEIGHTS | KEYWORDS |
| --- | --- |
| 0.006132082 | caveolin |
| 0.004281967 | kit |
| 0.002052745 | dpd |
| 0.00190056 | mast |
| 0.001568304 | mastocytosis |
| 0.00155767 | hsf |
| 0.001361383 | icc |
| 0.001161008 | adducin |
| 0.001126881 | tropomodulin |
| 0.001027287 | caveolae |
| 0.000914975 | syntaxin |
| 0.000914036 | hox |
| 0.000884391 | btk |
| 0.000863388 | tfiib |
| 0.000795634 | fyn |
| 0.00074206 | wee |
| 0.000691434 | kindling |
| 0.000666647 | ciita |
| 0.000600745 | fucose |
| 0.000548474 | fu |
| 0.000506843 | chop |
| 0.000476232 | sls |
| 0.000416166 | meis |
| 0.000395423 | ahr |
| 0.000365585 | rab |

CONCLUSION AND SCOPE OF INVENTION

While the above description contains may specifications, these should not be construed as limitations on the scope of the invention, but rather as an exemplification of preferred embodiments thereof.

The invention claimed is:

1. A system for annotating a group of subsets of genes with words and phrases that characterize each individual subset of genes and that also distinguish said individual subset of genes from each and every of the other individually characterized subsets of genes, by displaying words and phrases taken from literature abstracts and other text corresponding to each subset of genes, arranged in an order of sorted numerical weights that the system assigns to the words and phrases, comprising:

(a) means for identifying a set of genes;

(b) means for partitioning the set of genes in (a) into disjoint subsets of genes known as clusters;

(c) means for associating a set of literature documents with each gene in the set of genes in (a), and a means for receiving the text of part or all of each said literature document;

(d) means for constructing a compendium of text for each individual subset of genes known in (b) as a cluster, said compendium consisting of the text received for all of the literature documents that had been associated and received in (c), for all genes that are members of the subset of genes in said cluster;

(e) means for annotating the group of subsets of genes known as clusters in (b) by the Rainbow computer program, with words and phrases that characterize each individual subset of genes known as a cluster in (b) and that also distinguish said individual subset of genes from each and every of the other individually characterized subsets of genes known as a cluster in (b), in terms of different words and phrases that the system attaches to different individual subsets of genes, each of which is known as a cluster in (b), said annotating being performed in the following two stages:

first, instruct the computer program Rainbow to take as extrinsic input-data each and every compendium of text constructed in (d) for each individual subset of genes known in (b) as a cluster, then process said input-data to produce as output-data a statistical model of the text in all said compendia; and second, instruct the computer program Rainbow to take as its input-data the statistical model of the text, and to process that data to produce as output-data a list of words and phrases for each subset of genes known in (b) as a cluster, along with word-weights that Rainbow calculates for each word or phrase in the list, the magnitude of which indicates the weight that the system attaches to the corresponding word or phrase as a characterization of the subset of genes known in (b) as a cluster, said word-weights being calculated by default through Rainbow's implementation of the Naive Bayes algorithm, or optionally through Rainbow's implementation of other word weight-setting algorithms.

(f) means for sorting, pruning, storing, and displaying the words and phrases contained in a compendium of text constructed in (d), for each individual subsets of genes known as clusters in (b), said sorting being based on the magnitude of the numerical weights assigned to the corresponding words and phrases as provided in (e) for each subset of genes known as a cluster in (b); said pruning being based on the setting of a minimum cutoff for the magnitude of the numerical weights assigned to the corresponding words and phrases as provided in (e) for each subset of genes known as a cluster in (b); and said storing and displaying the pruned words and phrases, for each subset of genes known as a cluster in (b), arranged in descending order corresponding numerical weights;

whereby the words and phrases having the greatest numerical weights arranged in the descending order for each individual subset of genes known as a cluster in (b) provide an indication of the concepts, structures, functions, and processes with which said individual subset of genes known as a cluster in (b) is most associated with said cluster, and with which said individual subset of genes is also distinguished from each and every of the other individually characterized subsets of genes known as clusters in (b), in terms of different words and phrases that the system attaches to different individual subsets of genes known as clusters in (b).

* * * * *

UNITED STATES PATENT AND TRADEMARK OFFICE
CERTIFICATE OF CORRECTION

PATENT NO.         : 7,289,911 B1
APPLICATION NO.    : 09/934156
DATED              : October 30, 2007
INVENTOR(S)        : David Roth Rigney It is certified that error appears in the above-identified patent and that said Letters Patent is hereby corrected as shown below:

Title Page
In OTHER PUBLICATIONS, page 2, column 2, line 7, "~mccallum.bow" should be changed to -- ~mccallum/bow --.

Title Page
In OTHER PUBLICATIONS, page 2, column 2, line 21, "clasification" should be changed to -- classification --.

Column 1, line 35, cancel the text beginning with "Application No." to and ending "Sep. 20, 2006."

Column 2, line 63, "TAVAZONE" should be changed to -- TAVAZOIE --.

Column 3, line 11, "PEROUS" should be changed to -- PEROU --.

Column 3, line 15, "www.-sta," should be changed to -- www-stat, --.

Column 3, line 63, "the" should be changed to -- The --.

Column 5, line 21, "that" should be changed to -- than --.

Column 6, line 13, "form" should be changed to -- from --.

Column 7, line 51, "rainbow-d.\text_model—index.\clusters_text\*" should appear as follows: -- rainbow -d .\text_model --index .\clusters_text\* --.

Column 7, lines 59-60, the following line:
    "system("rainbow -d.\ \ text_model—index.\ \ clusters_text\ \*");"
  should appears as follows:
    -- system("rainbow -d .\\text_model --index .\\clusters_text\\*"); --.

Column 8, line 8, "researchers" should be changed to -- researcher --.

Column 8, line 15, "a alpha-numeric" should be changed to -- an alpha-numeric --.

Column 9, line 63, "To" should be changed to -- to --.

Column 10, line 38, "numbers" should be changed to -- number --.

UNITED STATES PATENT AND TRADEMARK OFFICE
CERTIFICATE OF CORRECTION

PATENT NO. : 7,289,911 B1
APPLICATION NO. : 09/934156
DATED : October 30, 2007
INVENTOR(S) : David Roth Rigney It is certified that error appears in the above-identified patent and that said Letters Patent is hereby corrected as shown below:

Column 10, lines 44-45, the following text:
 "path?query=/htbin—post/Omim/dispmim?"
 should appear as follows:
 -- path?query=/htbin-post/Omim/dispmim? --.

Column 10, line 66, "numeral" should be changed to -- numerals --.

Column 11, line 25, "parh?query=/htbin—post/Entrez/"
 should appear as follows:
 -- path?query=/htbin-post/Entrez/ --.

Column 11, line 34, "doamin" should be changed to -- domain --.

Column 13, line 19, "Backgroun" should be changed to -- Background --.

Column 13, line 25, "path/32" should be changed to -- path = --.

Column 13, line 58, "called \ clusters_text" should be changed to
 -- called \clusters_text --.

Column 13, line 65, "a Omim" should be changed to -- an Omim --.

Column 14, lines 6-7, the following text:
 "system("rainbow -d.\ \ text_model—index .\{clusters_text\ {*");"
 should appear as follows:
 -- system("rainbow -d .\\text_model --index .\\clusters_text\\*"); --.

Column 14, line 10, "called \ clusters_text" should be changed to
 -- called \clusters_text --.

Column 14, line 12, "called \ text_model" should be changed to -- called \text_model --.

Column 14, line 30, "rainbow—help" should appear as follows:
 -- rainbow --help --.

Column 14, line 53, "Chapter 6 or" should be changed to -- Chapter 6 of --.

Column 14, line 63, the following text:
 "system("…—method—METHOD…")"
 should appear as follows:
 -- system("…--method=METHOD…") --.

UNITED STATES PATENT AND TRADEMARK OFFICE
CERTIFICATE OF CORRECTION

PATENT NO. : 7,289,911 B1
APPLICATION NO. : 09/934156
DATED : October 30, 2007
INVENTOR(S) : David Roth Rigney It is certified that error appears in the above-identified patent and that said Letters Patent is hereby corrected as shown below:

Column 15, lines 4-5, the following text:
"system("rainbow -d.\ \text_model—print-word-weights=cluster_name>word-weights_cluster_anme.txt");"
should appear as follows:
-- system("rainbow -d .\\text_model --print-word-weights=cluster_name>word-weights_cluster_name.txt"); --.

Column 15, line 21, "Tables 1 and ' " should be changed to -- Tables 1 and 2 --.

Column 15, lines 29-30, "-d.\ \ text_model—print-log-odds-ration=20"
should appear as follows:
-- -d .\\text_model --print-log-odds-ratio=20 --.

Column 16, line 14, "points" should be changed to -- pointers --.

Column 16, line 33, "acession" should be changed to -- accession --.

Column 17, line 45, "may specifications" should be changed to -- many specifications --.

Column 18, line 39 of Claim 1, "each individual subsets" should be changed to
-- each of the individual subsets --.

Signed and Sealed this

Twenty Second Day of April, 2008

JON W. DUDAS
*Director of the United States Patent and Trademark Office*